United States Patent [19]

Edwards

[11] 3,996,243
[45] Dec. 7, 1976

[54] FUNGICIDAL 5-DIALKYLAMINO-4-NITROSULFONAMIDOTHIOPHENES

[75] Inventor: Laroy H. Edwards, Napa, Calif.

[73] Assignee: Chevron Research Company, San Francisco, Calif.

[22] Filed: May 19, 1975

[21] Appl. No.: 578,851

[52] U.S. Cl. .................. 260/329 S; 260/329 AM; 260/332.5; 424/275
[51] Int. Cl.² .................................. C07D 333/00
[58] Field of Search ..... 260/332.5, 329 S, 329 AM, 260/332.2 C; 424/275

[56] References Cited

UNITED STATES PATENTS

| | | | |
|---|---|---|---|
| 3,506,669 | 4/1970 | Laliberte | 260/332.2 C |
| 3,701,776 | 10/1972 | Pillon et al. | 260/332.5 |
| 3,707,480 | 12/1972 | Dunn et al. | 260/332.5 |

Primary Examiner—James O. Thomas, Jr.
Assistant Examiner—A. Siegel
Attorney, Agent, or Firm—George F. Magdeburger; Dix A. Newell; Raymond Owyang

[57] ABSTRACT

Novel thiophenes of the formula

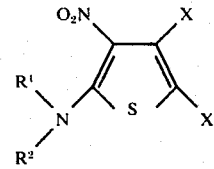

wherein $R^1$ is alkyl; $R^2$ is alkyl; one X is hydrogen, fluoro, chloro or bromo and the other X is —$SC_2N(R^3)(R^4)$ wherein $R^3$ is alkyl or aryl and $R^4$ is hydrogen or haloalkylthio, are useful for the prevention or cure of fungal infections.

9 Claims, No Drawings

FUNGICIDAL 5-DIALKYLAMINO-4-NITROSULFONAMIDOTHIOPHENES

DESCRIPTION OF THE PRIOR ART

French Pat. No. 1,563,736, issued Apr. 18, 1969, to Pillon et al, discloses pesticidal 2-sulfonamido-3,4,5-trichlorothiophenes. A. Buzas et al, "Ann. Pharm. France" 19, 499 (1961) [C.A. 56, 6603c (1962)] discloses diruretic 2-sulfonamidothiophenes.

DESCRIPTION OF THE INVENTION

The thiophenes of the invention are represented by the formula (I)

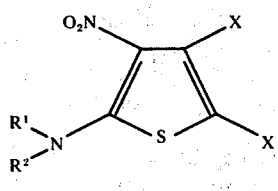

(I)

wherein $R^1$ is alkyl of 1 to 6 carbon atoms; $R^2$ is alkyl of 1 to 6 carbon atoms; one X is fluoro, chloro or bromo and the other X is $-SC_2N(R^3)$ $(R^4)$ wherein $R^3$ is alkyl of 1 to 6 carbon atoms or phenyl substituted with up to 2 (0 to 2) of the same or different substituents selected from trifluoromethyl, trichloromethyl, fluoro, chloro, bromo, nitro, or alkyl of 1 to 3 carbon atoms and $R^4$ is H or haloalkylthio of 1 to 3 carbon atoms and 1 to 7 of the same or different halogens of atomic number 9 to 35 (fluoro, chloro or bromo).

Representative alkyl $R^1$, $R^2$ and $R^3$ groups are methyl, ethyl, propyl, isopropyl, butyl and hexyl. Representative substituted phenyl $R^3$ groups are o-trifluoromethylphenyl, m-trifluoromethylphenyl, p-trichloromethylphenyl, o-fluorophenyl, m-chlorophenyl, p-bromophenyl, 2,4-dichlorophenyl, 3,5-dibromophenyl, 3-bromo-4-chlorophenyl, o-tolyl, 2,4-dimethylphenyl, p-nitrophenyl and 2-cloro-4-methylphenyl. Representative haloalkylthio $R^4$ groups are chloromethylthio, trifluoromethylthio, dichloromethylthio, trichloromethylthio, fluorodichloromethylthio, tribromoethylthio, 2,2,2-trichloroethylthio, 1,2,2,2-tetrachloroethylthio, 1,1,2,2-tetrabromoethylthio, pentachloroethylthio, 2,2,3,3,3-pentabromopropylthio and 3,3,3-trichloropropylthio.

The preferred $R^1$ and $R^2$ groups are alkyl of 1 to 3 carbon atoms, especially methyl. One X group preferably is hydrogen, chloro or bromo, and the other X group preferably is $SO_2N(R^3)(R^4)$ wherein $R^3$ is lower alkyl of 1 to 3 carbon atoms or phenyl substituted with up to 2 trifluoromethyl, fluoro, chloro or bromo and $R^4$ is hydrogen or polyhaloalkylthio of 1 to 2 carbon atoms and 2 to 5 of the same or different halogens selected from chloro or bromo. When X is hydrogen, it is preferably substituted at the 3 position of the thiophene ring. When X is fluoro, chloro or bromo, it is preferably substituted at the 2 position of the thiophene ring.

A preferred class of thiophenes of the formula (I) is that wherein one X is hydrogen, chloro or bromo, and the other X is $-SO_2N(R^3)$ $(R^4)$ wherein $R^3$ is alkyl of 1 to 3 carbon atoms or phenyl substituted with up to 2 trifluoromethyl, trichloromethyl, fluoro, chloro, bromo or alkyl of 1 to 3 carbon atoms and $R^4$ is hydrogen.

Another preferred class of thiophenes of formula (I) is that wherein one X is hydrogen, chloro or bromo and the other X is $-SO_2N(R^3)$ $(R^4)$ wherein $R^3$ is alkyl of 1 to 3 carbon atoms or phenyl substituted with up to 2 of the same or different substituents selected from trifluoromethyl, trichloromethyl, fluoro, chloro, bromo or alkyl of 1 to 3 carbon atoms and $R^4$ is polyhaloalkylthio of 1 to 2 carbon atoms and 2 to 5 of the same or different halogens selected from chloro or bromo.

The thiophenes of the invention wherein $R^4$ is hydrogen are prepared by reacting a 5-halo-4-nitrosulfonamidothiophene (II) with a dialkylamine compound (III). The thiophenes of the invention wherein $R^2$ is haloalkylthio are prepared by sulfenylating the resulting sulfonamidothiophene (IV) with a haloalkylsulfenyl halide (V) in the presence of an acid acceptor. These reactions are depicted in reactions (1) and (2) for a 2-sulfonamidothiophene or 3-sulfonamidothiophene (II).

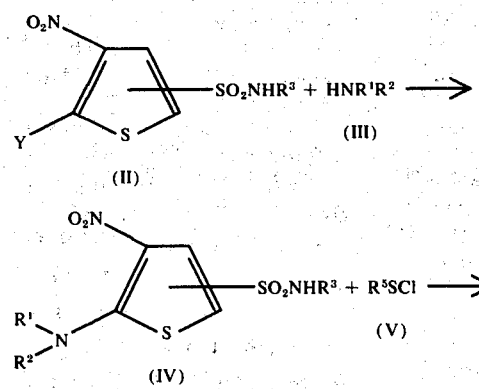

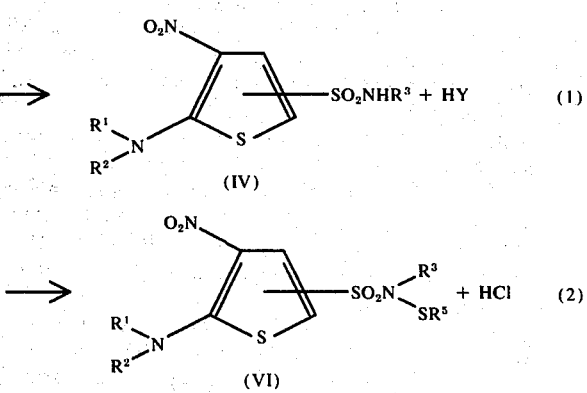

wherein $R^1$, $R^2$ and $R^3$ have the same significance as previously defined, $SR^5$ is a haloalkylthio $R^4$ group as previously defined, and Y is chloro or bromo.

Reaction (1) is conducted by reacting the sulfonamidothiophene (II) and the amine (III) in an inert diluent at a temperature of 0° to 100° C. Preferably a molar excess of the amine or aniline (III), or an acid acceptor as defined below, is used as an acid acceptor for the hydrogen halide produced in the reaction. Reaction (2) is conducted by reacting substantially equimolar quantities of the 5-dialkylamino-4-nitrosulfonamidothiophene (IV) and the sulfenyl chloride (V) in the presence of an acid acceptor. Suitable acid acceptors are organic amines such as pyridine compounds, e.g., pyridine or alpha-picoline, and lower trialkylamines, e.g., triethylamine or tripropylamine.

Generally, at least one mol of acid acceptor is employed for each mol of sulfenyl chloride. The reaction is normally conducted in an inert liquid diluent, e.g., organic solvents such as chlorinated hydrocarbons. The product (I) is isolated and purified by conventional procedures such as extraction, filtration, crystallization and chromatography.

The sulfonamidothiophenes of formula (II) are suitably prepared by reacting a 5-halo-4-nitrothienylsulfonyl chloride with an alkylamine ($NHR^3$) by conventional procedures. The 4-nitro-substituted thienylsulfonyl chloride reactants are suitably prepared by nitrating a thienylsulfonyl chloride with nitric acid in a suitable solvent such as concentrated sulfuric acid or acetic anhydride.

The compounds of the invention are useful for controlling fungi, particularly plant fungal infections caused by *Botrytis cinerea*, leaf blights caused by organisms such as *Septoria apii*, *Alternaria solani conidia* and *Phytophthora infestans conidia*, powdery mildew caused by organisms such as *Erysiphe polygoni* and *E. chicoraciarum*, and other fungal infections caused by organisms such as *Pythrium ultimum*, *Helminthosporum sativum*, *Fusarium moniliforme*, *Rhizoctonia solani*, *Monolinia fructicola* and *Uromyces phaseoli typica*. However, some fungicidal compounds of the invention may be more fungicidally active than others against particular fungi.

When used as fungicides, the compounds of the invention are applied in fungicidally effective amounts to fungi and/or their habitats, such as vegatative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents, and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier, such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of these these techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLES

EXAMPLE 1

Preparation of
5-dimethylamino-4-nitro-2-(N-methyl-N-1,1,2,2-tetrachloroethylthiosulfonamido)thiophene An 80-g (0.68 mol) sample of 2-chlorothiophene was added dropwise to a cooled (dry ice/acetone bath, about −10° to −15° C.) and stirred solution of 160 g (1.38 mol) of chlorosulfonic acid. After the addition was completed, the reaction mixture was stirred at 50° C for 2 hours, cooled, and then poured into 250 g of ice. The aqueous reaction mixture was extracted with methylene chloride. The methylene chloride extract was washed with saturated aqueous sodium bicarbonate solution, washed with water, dried over magnesium sulfate, and evaporated to give 40 g of 5-chloro-2-thienylsulfonyl chloride.

A 32.5-g (0.15 mol) sample of 5-chloro-2-thienylsulfonyl chloride was added in small portions to a stirred solution of 150 ml concentrated nitric acid and 150 ml concentrated sulfuric acid. After the addition was completed, the reaction mixture was stirred at about 25° C overnight. The reaction mixture was then diluted with ice water and filtered to give the 5-chloro-4-nitro-2-thienylsulfonyl chloride product.

A mixture of 20.2 g (0.2 mol) triethylamine and 26.2 g of a 40% aqueous methylamine solution (0.2 mol methylamine) was added dropwise to a cooled and stirred solution of 53.7 g (0.2 mol) 5-chloro-4-nitro-2-thienylsulfonyl chloride in 200 ml acetone. After completion of the addition, the reaction mixture was allowed to warm to 25° C and stirred for 2 hours. The acetone was removed by evaporation. The reaction mixture was then diluted with methylene chloride, washed with water, dried over magnesium sulfate, and evaporated to give the 5-chloro-4-nitro-2-(N-methylsulfonamido)thiophene product.

A 20.2-g (0.2 mol) sample of triethylamine was added dropwise to a cooled (0° C) solution of 25.7 g (0.1 mol) 5-chloro-4-nitro-2-(N-methylsulfonamido)-thiophene and 8.2 g (0.1 mol) dimethylamine hydrochloride in 200 ml methanol. The reaction mixture was then allowed to warm to about 25° C and heated at reflux for 2 hours. The reaction mixture was then evaporated to dryness under reduced pressure, diluted with methylene chloride, washed with water, dried over magnesium sulfate and evaporated to give an oil. The oil was crystallized from benzene to give 5-dimethylamino-4-nitro-2-(N-methylsulfonamido)thiopene, as dark green crystals.

A 6.6 g (0.0283 mol) sample of 1,1,2,2-tetrachloroethylsulfenyl chloride was added dropwise to a cooled (0° C.) solution of 7.5 g (0.0283 mol) 5-dimethylamino-4-nitro-2-(N-methylsulfonamido)thiophene in 150 ml methylene chloride. The reaction mixture was stirred at about 25° C for several hours, washed with water, dried over magnesium sulfate and evaporated to give the product as an oil which crystallized from hexane as a solid, m.p. 122°–124° C.

EXAMPLE 2

Preparation of
5-dimethylamino-4-nitro-2-chloro-3-(N-methyl-N-trichloromethylthiosulfonamido)thiophene A 96.8-g (0.632 mol) sample of 2,5-dichlorothiophene was added dropwise to a cooled (dry ice/acetone bath, about −10° to −15° C.) and stirred solution of 163 g (1.39 mol) of chlorosulfonic acid. After the addition was completed, the reaction mixture was stirred at 50° C for 2 hours, cooled, and then poured into 200 g of ice. The aqueous reaction mixture was extracted with methylene chloride. The methylene chloride extract was washed with saturated aqueous sodium bicarbonate solution, washed with water, dried over magnesium sulfate, and evaporated to give 87 g of 2,5-dichloro-3-thienylsulfonyl chloride.

A 55.8-g (0.22 mol) sample of 2,5-dichloro-3-thienylsulfonyl chloride was added in small portions to a stirred solution of 150 ml concentrated nitric acid and 150 ml concentrated sulfuric acid. After the addition was completed, the reaction mixture was stirred at about 25° C overnight. The reaction mixture was then diluted with ice water and filtered to give the crude 2,5-dichloro-4-nitro-3-thienylsulfonyl chloride product. The product was washed with water and dried. Recrystallization from methylene chloride gave the product as a brown solid, m.p. 89°–91° C.

A 30.4-g (0.33 mol) sample of aniline was added dropwise to a solution of 49.1 g (0.165 mol) 2,5-dichloro-4-nitro-3-thienylsulfonyl chloride in 250 ml methylene chloride cooled in a dry-ice/acetone bath (−50° C). The reaction mixture was then allowed to warm about 25° C and stirred at about 25° C overnight. The reaction mixture was filtered to remove the aniline hydrochloride salt. The filtrate was washed with water, dried over magnesium sulfate and evaporated to give 41 g 2,5-dichloro-4-nitro-3-(N-phenylsulfonamido)thiophene m.p. 127°–129° C.

A 12.2-g (0.122 mol) sample of triethylamine was added dropwise to a solution of 4.9 g (0.61 mol) dimethylamine hydrochloride and 21.5 g (0.61 mol), 2,5-dichloro-4-nitro-3-(N-phenylsulfonamido)thiophene in 200 ml methanol. The reaction mixture was heated under reflux for 3 hours. The methanol was then removed under reduced pressure and the residue was extracted with methylene chloride. The methylene chloride extract was washed with water, dried over magnesium sulfate and evaporated to give the crude 5-dimethylamino-4-nitro-2-chloro-3-(N-phenylsulfonamido)thiophene product. Crystallization from hexane gives the pure product as a brown solid, m.p. 143°–144° C.

A 2.3 g (0.023 mol) sample of triethylamine was added dropwise to a solution of 7 g (0.0194 mol) 5-dimethylamino-4-nitro-2-chloro-3-(N-phenylsulfonylamido)thiophene and 3.6 g (.0194 mol) trichloromethylsulfenyl chloride in 200 ml methylene chloride at −10° C. The reaction mixture was allowed to warm to about 25° C. and then heated under reflux for 1 hour. The reaction mixture was cooled, washed with water, dried over magnesium sulfate and stripped to give the 5-dimethylamino-4-nitro-2-chloro-3-(N-phenyl-N-trichloromethylthiosulfonamido)thiopene product as a brown solid, m.p. 140°–141° C.

Other compounds of the invention were prepared by procedures similar to that of Examples 1–2. These compounds and the compounds of Examples 1–2 are tabulated in Table I.

EXAMPLE 3

Bortrytis Cinerea Control 5-dimethyl-4-nitro-2-chloro-3-(N-methyl-N-trichloromethylthiosulfonamido)thiophene was tested for *Botrytis cinerea* control using detached, well-developed primary leaves of a 4–6 week old horsebean plant. The leaves were dipped into a 40-ppm solution of the test compound in acetone and water containing a small amount of a nonionic emulsifier, then taken out and placed in a petri plate lined with two pieces of filter paper. The leaves were allowed to dry while the fiber paper was kept moist by adding water as required. The treated leaves were then inoculated with the spores of *Botrytis cinerea* fungus grown on potato dextrose agar plates. The plates were covered after inoculation and kept at 23.5° C. The filter-paper linings of the plates were kept saturated with water throughout the test. The rate of disease incidence was determined in 3 to 5 days, when the disease symptoms were fully evident on nontreated check leaves. The percent disease control provided by the test compound was calculated as the percentage disease reduction based on the non-treated check leaves.

5-dimethylamino-4-nitro-2-chloro-3-(N-methyl-N-trichloromethylthiosulfonamido)thiophene was found to give 47% control.

EXAMPLE 4

Tomato Late Blight

Representative compounds of the invention were tested for the control of the Tomato Late Blight organism *Phytophthora infestans conidia*. Five-to-six-week-old tomato (variety Bonny Best) seedlings were used. The tomato plants were sprayed with a 250-ppm solution of the test compound in acetone, water, and a small amount of a non-ionic emulsifier. The sprayed plants were then inoculated one day later with the organisms, placed in an environmental chamber and incubated at 66°–68° F and 100% relative humidity for at least 16 hours. Following the incubation, the plants were allowed to dry and then were maintained at 60–80% relative humidity for approximately 7 days. The percent disease control provided by a given test compound was based on the percent disease reduction relative to untreated check plants.

By the above procedure, 5-dimethylamino-4-nitro-2-(N-methyl-N-trichloromethylthiosulfonamido) thiophene gave 84% control and 5-dimethylamino-4-nitro-2-(N-methyl-N-1,1,2,2,-tetrachloroethylthiosulfonamido)thiophene gave 64% control.

EXAMPLE 5

EXAMPLE 6

Celery Late Blight

Representative compounds of the invention were tested for the control of Celery Late Blight using celery (Utah) plants 11 weeks old. The Celery Late Blight organism was *Septoria apii*. The celery plants were sprayed with solutions of the candidate toxicant mixed with acetone, water and a nonionic emulsifier. The plants were then inoculated with the organism and placed in an environmental chamber and incubated at 66°–68° F in 100% relative humidity for an extended period of time (approximately 48 hours). Following the incubation, the plants were allowed to dry and then were maintained at a 60–80% relative humidity for approximately 14 days. The percent disease control provided by a given candidate toxicant is based on the percent disease reduction relative to untreated check plants.

By the above procedure, 5-dimethyl-4-nitro-2-(N-methyl-N-trichloroethylthiosulfonamido)thiophene gave 75% control, 5-dimethyl-4-nitro-2-(N-methyl-N-1,1,2,2-terachloroethylthiosulfonamido(thiophene) gave 91% control and 5-dimethyl-4-nitro-2-chloro-3-(N-methyl-N-1,1,2,2-tetrachloroethylthiosulfonamido)thiophene gave 68% control.

TABLE I

Compounds of the formula:

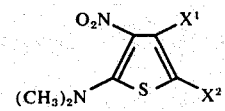

| Compound No. | $X^1$ | $X^2$ | Melting Point, °C | Elemental Analysis | | | |
|---|---|---|---|---|---|---|---|
| | | | | Sulfur | | Chlorine | |
| | | | | Calc. | Found | Calc. | Found |
| 1 | H | $SO_2N(CH_3)$ $(SCCl_2CCl_2H)$ | 122–124 | 20.8 | 20.7 | 30.6 | 28.6 |
| 2 | H | $SO_2N(CH_3)$ $(SCCl_3)$ | 131–132 | 23.2 | 22.6 | 25.7 | 24.2 |
| 3 | H | $SO_2N(iC_3H_7)$ $(SCCl_3)$ | 115–116 | 21.7 | 20.8 | 24.0 | 23.7 |
| 4 | H | $SO_2N(iC_3H_7)$ $(SCCl_2CCl_2H)$ | 127–128 | 19.6 | 19.4 | 28.9 | 27.6 |
| 6 | H | $SO_2N\phi$ $(SCCl_3)$ | 167–169 | 18.3 | 17.9 | 20.3 | 19.9 |
| 7 | H | $SO_2N(CH_3)$ $(SCCl_3)$ | 129–130 | 21.4 | 21.4 | 31.6 | 32.4 |
| 8 | $SO_2N(CH_3)$ $(SCCl_2CCl_2H)$ | Cl | 104–107 | 19.3 | 19.8 | 35.6 | 32.9 |
| 9 | $SO_2N\phi$ $(SCCl_3)$ | Cl | 140–141 | 18.8 | 17.1 | 27.7 | 26.3 |
| 10 | H | $SO_2NH(iC_3H_7)$ | 117–119 | 21.9 | 21.9 | — | — |
| 11 | $SO_2NH(CH_3)$ | Cl | 143–144 | 21.4 | 21.2 | 11.8 | 12.4 |
| 12 | $SO_2NH\phi$ | Cl | 143–144 | 17.6 | 18.6 | — | — |

$\phi$ = phenyl

Tomato Early Blight

Representative compounds of the invention were tested for the control of the Tomato Early Blight organism, *Alternaria solani* conidia. Tomato (variety Bonny Best) seedlings of 6 to 7 weeks old were used. The tomato plants were sprayed with a 250-ppm solution of the test compound in an acetone-and-water solution containing a small amount of a non-ionic emulsifier. The sprayed plants were inoculated one day later with the organism, dried and maintained at 60–80% relative humidity for about 12 days. Percent disease control was based on the percent disease development on untreated check plants.

By the above procedure, 5-dimethylamino-4-nitro-2-(N-methyl-N-1,1,2,2-tetrachloroethylthiosulfonamido)thiophene gave 68% control and 5-dimethyl-4-nitro-2-chloro-3-(N-phenyl-N-trichloromethylthiosulfonamido)thiophene gave 77% control.

What is claimed is:
1. A compound of the formula

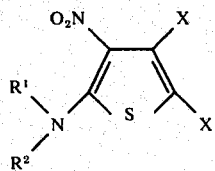

wherein $R^1$ is alkyl of 1 to 6 carbon atoms; $R^2$ is alkyl of 1 to 6 carbon atoms; one X is hydrogen, fluoro, chloro or bromo and the other X is $-SO_2N(R^3)$ $(R^4)$ wherein $R^3$ is hydrogen, alkyl of 1 to 6 carbon atoms, phenyl or phenyl substituted with 1 to 2 of the same or different substituents selected from trifluoromethyl, trichloromethyl, fluoro, chloro, bromo, nitro or alkyl of 1 to 3 carbon atoms and $R^4$ is haloalkylthio of 1 to 3 carbon atoms and 1 to 7 of the same or different halogens selected from fluoro, chloro or bromo.

2. The compound of claim 1 wherein $R^4$ is polyhaloalkylthio of 1 to 2 carbon atoms and 2 to 5 of the same or different halogens selected from chloro or bromo.

3. The compound of claim 2 wherein $R^4$ is trichloromethylthio or tetrachloroethylthio.

4. The compound of claim 2 wherein $R^3$ is alkyl of 1 to 6 carbon atoms.

5. The compound of claim 2 wherein the X group at the 3 position of the thiophene ring is hydrogen.

6. 5-dimethylamino-4-nitro-2-(N-methyl-N-1,1,2,2-tetrachloroethylthiosulfonamido)thiophene, according to claim 5.

7. The compound of claim 2 wherein the X group at the 2 position of thiophene ring is chloro or bromo.

8. 5-dimethyl-amino-4-nitro-2-chloro-3-(N-phenyl-N-trichloromethylthiosulfonamido)thiophene, according to claim 7.

9. 5-dimethylamino-4-nitro-2-(N-methyl-N-trichloroethylthiosulfonamido)thiophene, according to claim 5.

* * * * *